United States Patent
Eissa et al.

(10) Patent No.: US 9,863,962 B1
(45) Date of Patent: Jan. 9, 2018

(54) APTAMERS AND SENSING TECHNOLOGY USED FOR DETECTION OF GLYCATED HEMOGLOBIN IN WHOLE BLOOD

(71) Applicants: Shimaa Eissa, Riyadh (SA); Mohammed Zourob, Riyadh (SA)

(72) Inventors: Shimaa Eissa, Riyadh (SA); Mohammed Zourob, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 15/223,202

(22) Filed: Jul. 29, 2016

(51) Int. Cl.
| | |
|---|---|
| *C07H 21/02* | (2006.01) |
| *C07H 21/04* | (2006.01) |
| *G01N 33/72* | (2006.01) |
| *G01N 33/53* | (2006.01) |
| *C12N 15/115* | (2010.01) |

(52) U.S. Cl.
CPC ......... *G01N 33/723* (2013.01); *C12N 15/115* (2013.01); *G01N 33/5308* (2013.01); *C12N 2310/16* (2013.01); *G01N 2800/042* (2013.01)

(58) Field of Classification Search
CPC .............................. C12N 15/113; C12Q 1/6825
See application file for complete search history.

(56) References Cited

U.S. PATENT DOCUMENTS 9,494,582 B2 * 11/2016 Cameron ........... G01N 33/5308

* cited by examiner

*Primary Examiner* — Amy H Bowman
(74) *Attorney, Agent, or Firm* — Geeta Kadambi; Riddhi IP LLC

(57) ABSTRACT

High affinity DNA aptamers Seq ID#1-8 for HbA1C and tHb were successfully selected using SELEX after 11 rounds of selection. The tested aptamers bind to HbA1C with dissociation constants in the nanomolar range with the highest affinity aptamer, Seq ID#6, exhibiting a $K_d$ of 2.8 nM. Another aptamer sequence (Seq ID #4) which showed high binding affinity to tHb with a $K_d$ of 2.7 nM was also selected. The HbA1C and tHb-specific aptamers were then applied for the detection of HbA1C % using a voltammetric aptasensor array platform showing remarkable sensitivity and selectivity. The aptasensor array platform was validated using standard human whole blood samples and demonstrated linearity over wide concentration range. The developed platform is superior to current methodologies due to its simplicity, stability and lower cost which will facilitate the early and accurate diagnosis of diabetes.

12 Claims, 11 Drawing Sheets

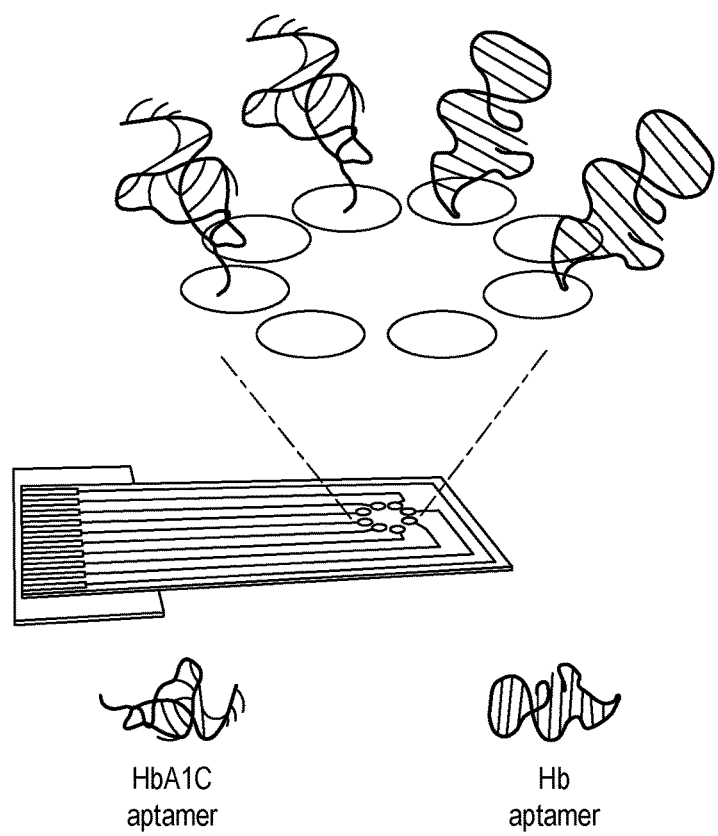
FIG. 4A
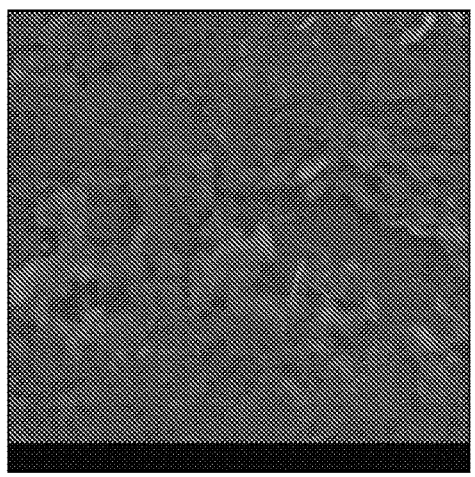 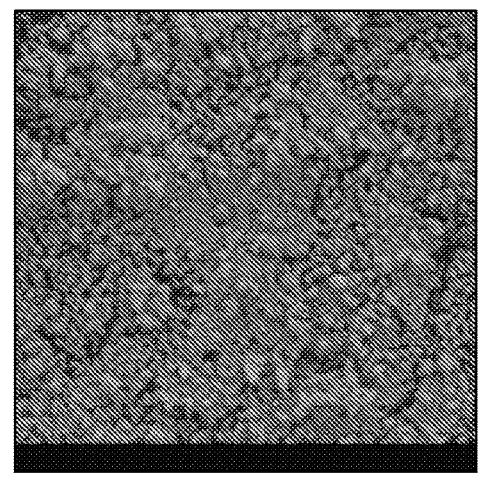
FIG. 4B            FIG. 4C

SEQUENCE LISTING

```
<160> NUMBER OF SEQ ID NOS: 9

<210> SEQ ID NO 1
<211> LENGTH: 60
<212> TYPE: DNA
<213> ORGANISM: Human

<400> SEQUENCE: 1
gggccgacgg gaggggagg gagagcaata cgaggtggga tggcagatta tgggtgcact    60

<210> SEQ ID NO 2
<211> LENGTH: 60
<212> TYPE: DNA
<213> ORGANISM: Human
<220> FEATURE:
<221> NAME/KEY: misc_feature
<222> LOCATION: (59)..(59)
<223> OTHER INFORMATION: n is a, c, g, or t

<400> SEQUENCE: 2
caccactcag cgacatcata tcatgaaaag cggagagcat ccgtgacgtg tggtttggnt    60

<210> SEQ ID NO 3
<211> LENGTH: 60
<212> TYPE: DNA
<213> ORGANISM: Human

<400> SEQUENCE: 3
cgacaccagc acacagaccc gagacacacg tcagatcaac agcgaccgta tcattggttg    60

<210> SEQ ID NO 4
<211> LENGTH: 60
<212> TYPE: DNA
```

```
<213> ORGANISM: Human

<400> SEQUENCE: 4
acgcacacca gagacaagta gcccccaaa cgcggccacg gaacgcagca cctccatggc      60

<210> SEQ ID NO 5
<211> LENGTH: 62
<212> TYPE: DNA
<213> ORGANISM: Human

<400> SEQUENCE: 5
ggccacagca gccagtacac ccacccacca gccccgtcaa cgacctgaac ctgccctgtg    60
tg                                                                  62

<210> SEQ ID NO 6
<211> LENGTH: 59
<212> TYPE: DNA
<213> ORGANISM: Human

<400> SEQUENCE: 6
ggggacacag caacacaccc acccaccagc cccagcatca tgcccatccg tcgtgtgtg     59

<210> SEQ ID NO 7
<211> LENGTH: 60
<212> TYPE: DNA
<213> ORGANISM: Human

<400> SEQUENCE: 7
cgcacaccag cacactcaaa agaacataca aagaacgtcg atccacatac cacggctgcc    60

<210> SEQ ID NO 8
<211> LENGTH: 59
<212> TYPE: DNA
<213> ORGANISM: Human

<400> SEQUENCE: 8
ggacacggca aagggtata gcctaccgga ccgtggacat ggaattgtgt gctgcgtgg      59

<210> SEQ ID NO 9
<211> LENGTH: 37
<212> TYPE: DNA
<213> ORGANISM: Human
<220> FEATURE:
<221> NAME/KEY: misc_feature
<222> LOCATION: (19)..(19)
<223> OTHER INFORMATION: n is a, c, g, or t

<400> SEQUENCE: 9
atatcatatg ctccaattna gatcgcaagt gtaatat                             37
```

APTAMERS AND SENSING TECHNOLOGY USED FOR DETECTION OF GLYCATED HEMOGLOBIN IN WHOLE BLOOD

CROSS REFERENCE TO SEQUENCE FILE

This application contains sequence listing that has been submitted as an ASCII file named RIPLLC032.008US1_ST25correct, the date of creation Apr. 6, 2017, and the size of the ASCII text file in bytes is 2 kb.

FIELD OF TECHNOLOGY

This disclosure relates generally to detecting glycated hemoglobin and total hemoglobin in human whole blood using specific aptamer based sensing technology.

BACKGROUND

Diabetes mellitus is a life-long metabolic disease that can cause several complications representing one of the most important health concerns nowadays. The early diagnosis of Diabetes and regular monitoring of blood glucose level are essential factors in preventing the health complications resulting from this disease. Glycated hemoglobin is an adduct that results from the non-enzymatic reaction of glucose with the N-terminal valine of hemoglobin β-chains. A build-up of glycated hemoglobin within the red blood cell, therefore, reflects the average level of glucose to which the cell has been exposed during its life-cycle and can serve as a marker for average blood glucose levels over the previous months prior to the measurement (J. Y Park et. al. 2008, E. S. Kilpatrick, 2008). In contrast to the common plasma glucose tests, the level of glycated hemoglobin is not influenced by daily fluctuations in the blood glucose concentration but reflect the average glucose levels over the prior six to eight weeks (Goldstein et. al., 2004).

Glycated hemoglobin testing is recommended for checking blood sugar in people who might be pre-diabetic. In fact, the 2010 American Diabetes Association (ADA) added the blood concentration of glycated hemoglobin (HbA1c) of over 6.5% as another criterion for the diagnosis of diabetes (American care 2010). Screening of elevated HbA1c level to a broader population represent an effective way for early diagnosis of diabetes. Higher amounts of HbA1c not only indicate poorer control of blood glucose levels, but also associates with cardiovascular disease, nephropathy, and retinopathy, emphasizing the importance of the precise and accurate monitoring of HbA1C %. Furthermore, monitoring the HbA1c in type-1 diabetic patients may improve treatment (American care 2014).

Current methodologies for HbA1c detection are mainly based on either charge differences (chromatography) (Lafferty J. D. et. al., 2002), structure (affinity or immunoassay assays) or enzymatic assays with the aim to differentiate between HbA1C and native Hb. According to the results of the GH-2 survey of the HbA1c test done by the College of American Pathologists (CAP, USA), immunoassays are the most commonly used methods (65% of participants) followed by the cation-exchange chromatography (31%) then the affinity chromatography (4%). In the chromatography-based methods, the HbA1c % is photometric determined by measuring the ratio of the HbA1c peak area over the tHb peak area. Thus, false positive or negative results can be obtained using these methods due to the possible interferents from the blood (Little R. R. et. al. 2013). Moreover, these methods are generally carried out in centralized laboratories using large and expensive instruments. Several immunoassays have been used for the quantification of HbA1C % using specific mono- or polyclonal antibodies to HbA1C (Wang, B. 2015). Separate ELISA kits based on sandwich assays for the detection of both HbA1c and tHb are commercially available. However, these kits are not intended to produce results for clinical use and cannot be accurately utilised for HbA1C % detection. Immunoassays based on field effect transistor (Qu. L, et. al. 2008) or electrochemical detection using boric acid-modified electrode have been reported (Song S. Y., et. al. 2009). However, the borate-modified electrodes can recognise the blood albumin causing interference. Some sandwich assays using specific HbA1c antibody as capture probe and such lectin or glycan-binding antibodies as detection probe have been reported (Kuno, A. et. al. 2005). However, this method suffers from low sensitivity due the interference from other glycan moieties in the blood sample and the high background signal. In other study, a polyclonal antibody against Hb was used as a common capture probe which binds to all forms of Hb and specific monoclonal antibodies against tHb and GHbA1c were used as detection probes (Chen S. S. et. al. 2012). This immunosensor fabricated using microarray system has eliminated the use of glycan binding molecules and thus, significantly reduced the background interference, achieving high sensitivity. However, immunoassays in general suffers from the instability of the antibodies, their high cost, batch-to-batch variations which limits the clinical usefulness of these methods (Max. V. 2013). Therefore, the development of low cost, stable, portable, specific and simple biosensing platform for the detection of HbA1c is highly demanded and would facilitate the routine monitoring of HbA1c % in blood for the early diagnosis of diabetic patients.

Aptamers are short single stranded DNA (ssDNA) or RNA sequences that have been recently appeared (Ellington A. D. et. al. 1990) as novel recognition receptors which can be used as alternative to antibodies in biosensing devices. Aptamers can be selected in vitro against a variety of targets including small molecules, metal ions and proteins using a process known as SELEX (Sampson, T. 2003). Because of their high affinity and stability, low cost and ease of synthesis with high reproducibility, DNA aptamer are being used as recognition elements replacing antibodies in many biosensing platforms. Recently, Lin H. I. et al. (2015) have reported the first identification of specific aptamers against HbA1c and tHb using microfluidic SELEX chip from a randomized 40-mer DNA library. In this report, the authors have shown a preliminary application of the selected aptamers in an aptamer-antibody sandwich-like chemiluminescence immunoassay. However, the selection of other aptamer sequences for Hb and HbA1C gives a diversity in applying different aptamers that have different molecular structures in a variety of biosensing platforms (McKeague M, et. al. 2014).

Accordingly, there is still a need to develop simple, sensitive, specific, rapid, cost-effective point of care capability of detecting the presence glycated hemoglobin and total hemoglobin in human whole blood.

SUMMARY

The present disclosure describes an aptamer and sensing technology used for detecting glycated hemoglobin and total hemoglobin in whole blood of human.

In one embodiment, a method of using an aptamer sequence for diagnosing a disease is disclosed. Whole human blood without any pretreatment is collected. A 60-mer DNA aptamer sequence against a glycated hemoglobin and total hemoglobin is selected in another embodiment.

In one embodiment, the selection of DNA aptamers is done using SELEX process or any other process that suits the array selection is used.

In one embodiment, wherein the 60-mer DNA aptamer consists of Seq ID #4 and Seq ID #6 were used to build an aptamer array. The aptamer sequences may be made in full or part of it may be used for binding studies. In another embodiment, the aptamer array is integrated with a sensing platform, wherein the sensing platform is at least one of an optical (fluorescence, refractive index changes), electrochemical, mass-sensitive, thermal sensor or any other type of sensing device. As a method the whole human blood after dilution is added to the aptamer array. In another step of the method the aptamer array is incubated with the whole blood diluted sample for 30 minutes at room temperature and washing with a buffer solution to remove unbound whole blood sample; and finally a concentration of a total hemoglobin and glycated hemoglobin in the whole blood using the sensing platform to estimate the said concentration of total hemoglobin and glycated hemoglobin is performed.

In one embodiment, wherein the dilution of the whole blood is done sequentially using a deionized water and a binding buffer.

In one embodiment, wherein the aptamer having a sequence is Seq ID#4.

In one embodiment, wherein the aptamer having a sequence is Seq ID#6.

In one embodiment, a method of using an aptamer sequence for diagnosing a disease, comprises of creating an aptamer array of 60-mer DNA comprising of Seq ID #4 and Seq ID #6 contacting the aptamer array with a whole blood sample of a human being; and estimating the concentration of a conjugate of the aptamer and a specific parameter that is bound to the aptamer using a sensing platform for the diagnosis of the disease.

In one embodiment, wherein the human disease is diabetes, wherein the specific parameter is total hemoglobin and glycated hemoglobin.

In one embodiment, an aptamer array containing essentially Seq ID #4 and Seq ID #6 DNA sequences to detect a specific parameter in a human whole blood using a sensing platform. Only microliter samples of blood are used after dilution.

In another embodiment, wherein the specific parameter is a total hemoglobin and glycated hemoglobin.

In one embodiment, wherein the Seq ID#4 is used for a total hemoglobin detection.

In one embodiment, wherein the Seq ID#6 is used for a glycated hemoglobin detection.

In another embodiment, wherein the sensing platform is at least one of an optical (fluorescence, refractive index changes, colorimetric), electrochemical, mass-sensitive, thermal sensor or any other type of sensing device.

In one embodiment, wherein the aptamer array has a gold nanoparticle.

In one embodiment, wherein the sensing platform is electrochemical using a squarewave voltammetry measurements to detect the specific parameter.

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

FIG. 4A Schematic diagram of the aptasensor array platform and scanning electron microscopic image of the screen printed carbon electrodes before FIG. 4B and after FIG. 4C shows AuNPs deposition.

Figure 1:
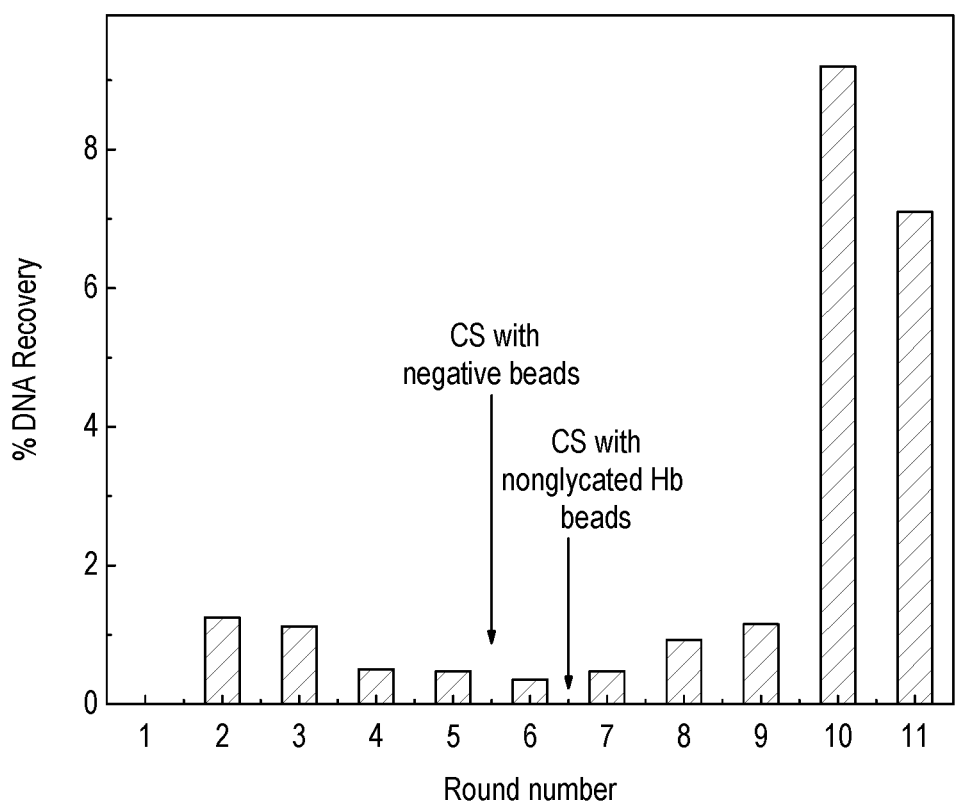
FIG. 1 shows DNA recovery during the SELEX screening against HbA1C.

Other features of the present embodiments will be apparent from the accompanying drawings and from the detailed description that follows.

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the description may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

In the normal 120-day lifespan of the red blood cell, glucose molecules react with hemoglobin, accumulating an adduct known as glycated hemoglobin (HbA1C)1. As the average amount of blood glucose increases, the fraction of glycosolated hemoglobin increases in a predictable way. Therefore, the percentage of HbA1C % in blood can serve as a marker for average blood glucose level over the past three months and thus, it can be used to diagnose diabetes. However, the quantification of HbA1C in whole blood using immunoassays remains a major challenge due the high cost of antibodies and their limited stability. Here, we report the selection, identification and characterization of specific DNA aptamers against HbA1c- and total hemoglobin (tHb) and their integration into an electrochemical microarray sensing platform. High affinity and specificity aptamers for HbA1c- and tHb were selected using systematic evolution of ligand by exponential enrichments (SELEX) protocol. Electrochemical impedance spectroscopy was utilised to investigate the affinity and specificity of the selected aptamers to their targets showing dissociation constants of 2.8 and 2.7 nM for HbA1c and tHb, respectively. Thiol-modified forms of the selected aptamer sequences were then immobilised on gold nanoparticles (AuNPs)-modified microarray electrodes and used for the label-free detection of HbA1c and tHb. The binding of the HbA1c and tHb to their specific aptamers leads to a decrease in $[Fe(CN)_6]^{3-/4-}$ reduction peak current that was monitored using square wave voltammetry. The label-free voltammetric aptasensors showed high sensitivity with detection limits of 0.2 and 0.34 ng/ml for HbA1c and tHb, respectively. This microarray platform is superior to the currently available immunoassays in terms of simplicity, stability, ease of use, reduction of sample volume and low cost. Moreover, this method enabled the detection of HbA1c % in human whole blood without any pre-treatment, suggesting the great promise of this platform for the diagnosis of diabetes.

Materials and Reagents:
The DNA library (5'-ATA TCA TAT GCT CCA ATT-N$_{60}$-

AGATCGCAAGTGTAATAT-3') (Seq ID#9), primers for polymerase chain reaction (PCR), and the aptamer sequences were custom-synthesized by Integrated DNA Technologies Inc. (Coralville, USA). The thiol modified aptamers are G20 (Seq ID#6): 5'HS- (CH2)6/
GGGGACACAGCAACACACCCACCCACCAGCCCCAGCATCATGCCCATCCG TCGTGTGTG-3'
and G15 (Seq ID #4): 5'HS- (CH2)6/
ACGCACACCAGAGACAAGTAGCCCCCCAAACGCGGCCACGGAACGCAGCA

CCTCCATGGC -3')

Sodium carbonate anhydrous, sodium bicarbonate, sodium azide, Taq plus DNA polymerase, acrylamide/bis-acrylamide (40% solution), urea, Tris-base, boric acid, EDTA disodium dehydrate, methanol were purchased from Bioshop Inc. (Ontario, Canada). TOPO TA Cloning Kit with One Shot MAX Efficiency DH5α-T1, 3,3',5,5'-tetramethylbenzidine (TMB) stabilized chromogen and HRP-labeled IgG antibody were purchased from Invitrogen (NY, USA). N-hydroxysuccinimide (NHS)-activated Sepharose™ beads, Potassium ferrocyanide ($K_4Fe(CN)_6$), potassium ferricyanide ($K_3Fe(CN)_6$), dipotassium hydrogen orthophosphate, potassium dihydrogen orthophosphate, sodium chloride, magnesium chloride, sulphuric acid, cysteamine hydrochloride, 1,4-phenylene diisothiocyanate (PDITC), N,N-dimethyl formamide (DMF), pyridine, bovine serum albumin (BSA), acetic acid, sodium acetate, potassium nitrate, mercapto-1-hexanol (MCH) and gold (III) chloride (HAuCl4) solution were purchased from Sigma (Ontario, Canada). Purified HbA1C, Hb and anti human HbA1c antibody were obtained from Monojo (Amman Jordan). The quality control Samples (LN15-08-LN15-11) prepared from pooled whole blood from healthy or diabetic individuals were obtained from College of American Pathologists. Amicon Ultra-0.5 mL Centrifugal desalting Filters with a 3 kDa molecular cut-off were obtained from EMD Millipore (Alberta, Canada). Centrifuge tube filters with a cellulose acetate membranes with pore size of 0.45 µm were purchased from Corning life sciences (Tewksbury M A, USA). Binding buffer which was used during the aptamer selection consists of 50 mM Tris, pH 7.5, 150 mM NaCl, 2 mM $MgCl_2$. Elution buffer is 7 M urea in binding buffer. Tris-EDTA buffer (TE) is 10 mM Tris, pH 7.4, 1 mM EDTA. A 10 mM phosphate buffered saline (PBS) solution (pH 7.4) was used for the ELISA experiments. 0.1 M $NaHCO_3$, 0.5 M NaCl, pH 8.3 was used for the coupling of HbA1C and Hb to the NHS activated sepharose beads. The 1,4-phenylene diisothiocyanate solution was prepared by dissolution in pyridine and N,N-dimethyl formamide (DMF) (v:v, 1:9). All solutions were prepared using Milli-Q grade water.

Instrumentation: Electrochemical experiments were performed using Autolab PGSTAT302N (Eco Chemie, The Netherlands) potentiostat/galvanostat, controlled by Nova 1.11 software. A three-electrode system was used for the binding affinity measurements, consisting of a gold working electrode, an Ag/AgCl electrode as the reference and a Pt wire as the auxiliary electrode. The electrochemical biosensing experiments were done using disposable electrical printed (DEP) microarray electrodes from BioDevice Technology (Nomi, Japan). The microarray electrode consists of eight individually addressable carbon working electrodes, a ring-shaped carbon auxiliary electrode, and a central silver/silver chloride reference electrode. A sensor connector (BioDevice Technology) is used to connect the DEP electrodes to the Autolab potentiostat. The UV and fluorescence measurements were performed using NanoDrop 2000C Spectrophotometer and NanoDrop 3300 Fluorospectrometer, respectively (Fisher Scientific, Canada).

Methods

Figure 8:
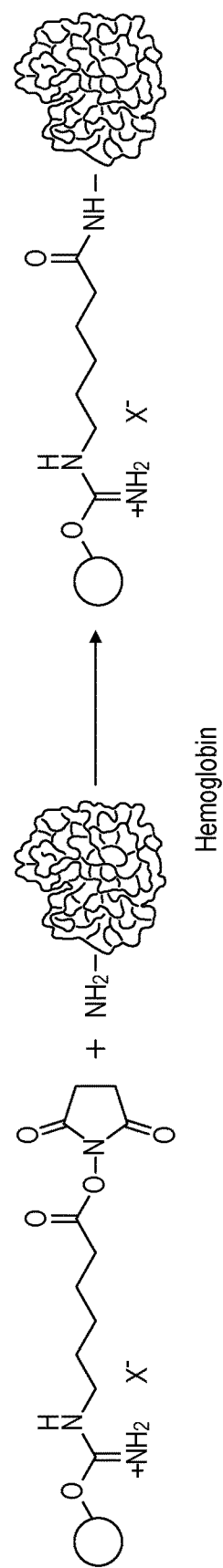
FIG. 8 shows attachment of Hb and HbA1C to NHS activated beads.

Coupling of HbA1C and tHb to the NHS activated beads: The coupling reaction is shown in the schematic diagram (FIG. 8). Stock solutions of purified Hb (363 µg) and HbA1C (1.9 mg) in coupling buffer (0.1 M $NaHCO_3$, 0.5 M NaCl, pH 8.3) were prepared. Two milliliters of the NHS activated beads were washed for 15 min with 1 mM HCL to remove the additives and preserve the activity of the reactive groups. The washed beads were then added to the stock solution of either Hb or HbA1C (1:1 volume ratio) in polypropylene tubes and gently mixed end-over-end for 4 hours at 4° C. After the reaction, the beads were washed five times with coupling buffer to remove the excess proteins. The unreacted NHS active groups on the beads were then blocked by transferring the beads to 0.1 M Tris-HCL buffer pH 8 and mixing for 1 hour. After that the beads were washed extensively with three cycles of alternating pH. Each cycle consists of a wash with 0.1 M acetic acid/sodium acetate, pH 4 containing 0.5 M NaCl followed by a wash with 0.1 M Tris-HCL buffer pH 8 containing 0.5 M NaCl. Simultaneously, negative NHS activated beads were also blocked using 0.1 M Tris-HCL buffer pH 8 in order to use it for the counter selection rounds. Finally, the Hb beads, HbA1C beads and the negative beads were stored in 50 mM Tris-HCl buffer pH 7.5 at 4° C. until further use. The success of the immobilization of Hb and HbA1C on the beads was confirmed by performing direct ELISA for the coupled beads and the negative beads as control. To perform the ELISA experiments, 30 µl of each beads were washed with PBS buffer pH 7.4 and blocked with 2% BSA in PBS buffer overnight at 4° C. Then the beads were incubated with diluted anti-HbA1C antibody (1:1000) in PBS buffer, pH 7.4. After washing, the beads were incubated with HRP-labelled secondary antibody (diluted 1:1000) for 1 h. Then the beads were washed three times with PBS buffer and stabilized chromogen (TMB) solution was added. A blue color was produced in the HbA1C-coated beads, while no color was observed in the Hb coated beads as well as in the negative beads indicating the success of the coupling reaction. The stability of the Hb and HbA1C-beads were also confirmed by ELISA after storage for few weeks during the SELEX process.

In vitro selection of the DNA Aptamer: A random ssDNA library (3 nmol or $1.8 \times 10^{15}$ sequences) was used for the SELEX experiments which consists of a central random region of 60 nucleotides flanked by two fixed regions of 18 nucleotides-sequences at the 3' and 5' ends. These regions represent the primer binding sites for the amplification (5'-ATA TCA TAT GCT CCA ATT-$N_{60}$-

AGATCGCAAGTGTAATAT-3') (Seq ID#9).

100 µl of HbA1C-beads were washed several times with binding buffer. (3 nmol at the first selection round, and 150 pmol in the subsequent rounds) of ssDNA pool were heated to 90° C. for 5 minutes, cooled at 4° C. for 10 minutes, kept at 25° C. for 5 minutes and then added to the washed HbA1C-beads in 300 µL binding buffer in a centrifuge filter tube. The mixture was incubated at room temperature with end-over-end rotation for 2 hours. The beads were then washed several times with binding buffer. Then, the DNA bound to HbA1C-beads was eluted with 400 µL aliquots of elution buffer 6 times with heating at 90° C. for 10 minutes until no DNA is detected in the fluorescence measurements. The eluted DNA was concentrated and desalted by ultrafiltration device. In a counter selection round, the DNA pool was first incubated with the negative beads, washed DNA was collected, subjected to the same heating and cooling treatment and subsequently incubated with HbA1C-beads. Another counter selection round was performed by incubating the DNA pool with Hb-beads and the washed DNA was again collected and incubated with HbA1C-beads. The selected DNA pool after each round was amplified by PCR in 15 parallel 75 µL reactions each containing 2 units of Taq Plus and polymerase buffer, 2 mM $MgCl_2$, 200 µM dNTP, 0.2 µM of forward and reverse primers. The primers were modified with fluorescein and a PEG linker followed by a poly-A tail as reported previously (Ng. A., et. al. 2012, Eissa, S. et. al., 2013, Eissa S, et. al., 2015). Forward primer: 5'-fluorescein-ATATCATATGCTC-CAATT-3'; reverse primer: 5'-poly-$dA_{20}$-$PEG_6$-ATATTA-CACTTGCGATCT-3'. PCR conditions: 94° C. for 10 minutes, followed by 25 cycles of 94° C. for 1 minute, 47° C. for 1 minute, 72° C. for 1 minute, and a final extension step of 10 minutes at 72° C. PCR products were dried by SpeedVac, resuspended in water and formamide (50:50 v/v) and heated to 55° C. for 5 minutes. The relevant DNA strand (labelled with fluorescein) was separated from the double stranded PCR product in 12% denaturing PAGE and eluted from the gel band by freeze-thaw cycle. Eluted ssDNA in TE buffer was concentrated, desalted by ultrafiltration, quantified by UV and used for the next selection round. The aptamer sequences may be made in full or part of it may be used for binding studies.

Cloning and Sequencing of Selected DNA:

After eleven selection rounds where DNA recoveries began to plateau as monitored by measuring the fluorescence of the eluted DNA, the selected ssDNA were amplified with the non-modified primer set and cloned into pCR2.1-TOPO vector using the TOPO TA Cloning Kit. Colonies were grown on LB-agar medium supplemented with ampicillin, X-Gal and IPTG. Positive colonies were picked and grown in liquid media. ssDNA inserts were PCR amplified using the M13 forward and reverse primer sites within the vector and sequenced. Sequences of the selected ssDNAs were analyzed and aligned using PRALINE Simossis V. A. et. al. 2005).

Immobilization of Hb and HbA1C on the gold electrode: The polycrystalline Au electrodes were polished with aqueous alumina slurries of 1 mm, 0.05 mm, then rinsed with water. The electrodes were then cleaned with fresh Piranha's solution (1:3 v/v, $H_2O_2$ and $H_2SO_4$) for 2 min. and subsequently washed with Milli-Q water and ethanol. Finally, the Au electrodes were subjected to electrochemical cleaning by cyclic voltammetry cycling between 0.20 and 1.6 V vs. Ag/AgCl (3M KCl) at 100 mV/s in 0.1 M sulphuric acid until the characteristic CV of a clean gold is obtained. After cleaning, the gold electrodes were immersed in 10 mM cysteamine hydrochloride for 2 hours at room temperature to form self-assembled monolayers. The electrodes were then washed with water and absolute ethanol to remove unbounded cysteamine residues. The terminal amine groups of cysteamine modified gold electrode (Cys/Au) were then activated by immersing the electrode in 10 mM PDITC in pyridine and N,N-dimethyl formamide (v:v, 1:9) for 2 h. Then, the electrodes were washed with DMF, ethanol and dried. The PDITC-modified electrodes were then incubated in 10 µg/ml of Hb or HbA1C solution in PBS buffer pH 7.4 for 2 h and then rinsed with PBS buffer to remove the unbound proteins. The modified electrodes were immersed in 1% BSA in PBS buffer (pH 7.4) for 30 min to deactivate the remaining thiocyanate groups and block the free gold surface, and then extensively washed with PBS buffer. The control aptasensor was prepared by incubating the PDITC-modified electrode with 3% BSA in PBS buffer (pH 7.4) for 2 hours. The Hb and HbA1C-modified electrodes were washed with PBS buffer and stored at 4° C. in PBS buffer until further use.

Binding analysis of the aptamer sequences to Hb and HbA1C: In order to test the binding affinity of the aptamer sequences to their protein targets, some representative sequences were synthesized after eliminating the primers sequence. A solution of 25 nM from each aptamer sequence in binding buffer was incubated with the Hb and HbA1C-modified electrodes (described in section 2.3.4) for 30 min. The electrodes were then washed with binding buffer and impedance measurements were recorded in 5 mM $[Fe(CN)_6]^{3-/4-}$ redox couple. The binding was then evaluated by calculating the % $R_{CT}$ change)((R−R°/R°%).

Dissociation constants determination by electrochemical assay: The dissociation constants of the selected aptamers for Hb and HbA1C were determined by performing binding assays as described above using various concentrations of the aptamer (0 to 200 nM). The change in the $R_{CT}$ after binding with each aptamer sequence was measured and saturation curve was obtained for each aptamer. The dissociation constant ($K_d$) for each sequence with HbA1C and Hb was calculated by non-linear regression analysis.

Microarray Electrodes Modifications and Aptasensors Fabrication:

The eight carbon working electrodes of the array chip were modified with gold nanoparticles (AuNPs). The chip was covered with 100 μl of 6 mM $HAuCl_4$ solution in 0.1 M $KNO_3$ and electrodeposition was performed using 20 cyclic voltammetry scans from −0.2 to −1.2 V at 50 mV/s.

For immobilization of aptamers, the thiol-modified Hb aptamer (G15) and HbA1C aptamer (G20) solutions in binding buffer were incubated separately onto different AuNPs-modified electrodes on the microarray chip for 12 h at water saturated atmosphere. After immobilization, the electrodes were washed with binding buffer and incubated with 1 mM MCH in PBS buffer, pH 7.4 for 30 min. The modified electrodes (aptasensors) were then washed thoroughly with binding buffer and immediately used in the electrochemical experiments, or kept in binding buffer solution at 4° C. until further use.

Electrochemical measurements: For the binding affinity studies, electrochemical impedance spectroscopy (EIS) was recorded over a frequency range from 10 kHz to 1.0 Hz using an alternative voltage with amplitude of 10 mV, superimposed on a DC potential of 0.20 V (vs a Ag/AgCl reference electrode). The impedance data were plotted in the form of complex plane diagram (Nyquist plot). The obtained spectra were fitted using Nova 1.11 software. All the EIS measurements were recorded in a 0.1 M PBS buffer solution containing 5 mM $[Fe(CN)_6]^{3-/4-}$ redox pair (1:1 molar ratio).

For the Hb and HbA1C detection and selectivity experiments, each aptamer-modified electrode on the aptasensor array chip was incubated for 30 min with specific concentrations of Hb and HbA1C standard solutions. The electrodes were then washed with 50 mM Tris-HCl buffer pH 7.4 and subjected to square wave voltammetry (SWV) measurements in 10 mM $[Fe(CN)_6]^{3-/4-}$ redox couple in 0.1 M PBS buffer solution. The parameters used for the SWV measurements: amplitude 20 mV; interval time 0.04 s; step potential −5 mV; scan rate 125 mV s-1, and frequency 25 Hz. The cyclic voltammetry (CV) experiments were conducted at a scan rate of 100 mV/s.

Application of the aptasensors in standard human whole blood samples: Quality control Samples (LN15-08-LN15-11) of human whole blood obtained from College of American Pathologists were used to validate the aptasensor. The concentrations of HbA1C in the samples are: LN15-08: 6.67%, LN15-09: 7.94%, LN15-10: 9.18% and LN15-11: 10.47%. The four blood samples were serially diluted by orders of magnitude ranging from $10^{-2}$ to $10_{-5}$ with deionized water (1 μl of blood was diluted to 100 μl with deionized water and the next dilutions were done in binding buffer). 2 μl of each diluted blood sample were then incubated on different spots of the Hb and HbA1C modified aptasensor array and kept for 30 min at room temperature. Then the electrodes were washed with 50 mM Tris-HCl buffer pH 7.4 and subjected to SWV measurements as previously described.

Results and Discussion

Immobilization of hemoglobin and glycated hemoglobin-A1C on the NHS-activated sepharose beads: The immobilization of target proteins on solid matrix is essential step in order to separate the bound from unbound DNA sequences during the SELEX process. Here, we coupled Hb and HbA1C proteins to commercial sepharose beads via the reaction of the NHS terminal of the beads with the amine groups of the proteins (FIG. 8). The coupling reaction was then confirmed using direct ELISA. The blue color observed in the HbA1C-beads indicated the success of the covalent immobilization.

Figure 9:
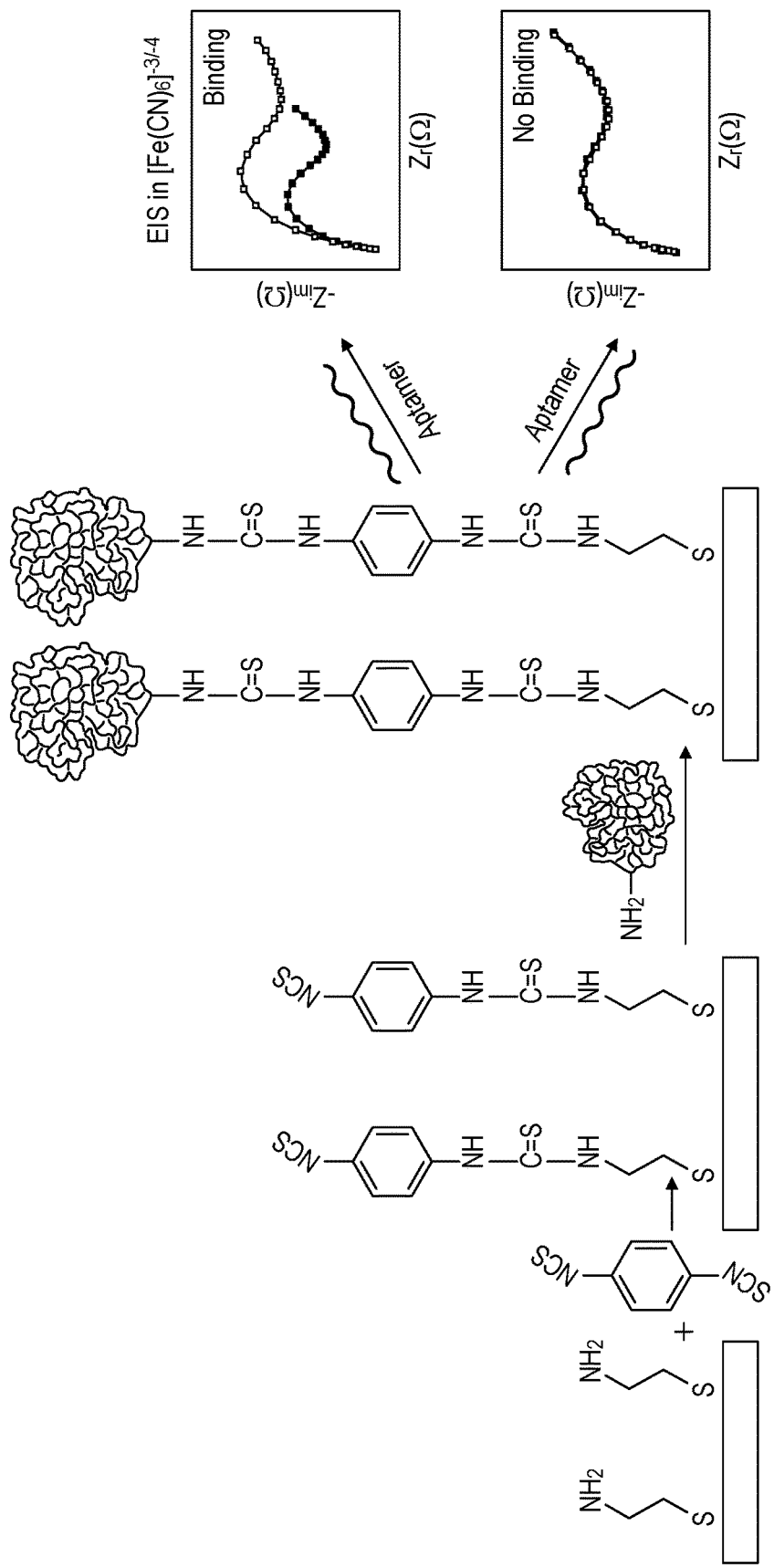
FIG. 9 shows schematic diagram of the gold electrode modification and immobilization of Hb and HbA1C proteins for the binding affinity studies.

In Vitro Selection of the DNA aptamers against HbA1C: A SELEX protocol was performed for the selection of specific aptamers to HbA1C. The aptamers should specifically recognise the glucose-bound amino acids at the N-terminal of the β-chain of Hb in order to have the capability to distinguish the glycated from the non glycated Hb. The selection of the aptamers was performed following the protocol that we reported previously. A DNA library consisting of $1.8 \times 10^{15}$ random sequences were incubated with the HbA1C-beads followed by a separation step of the bead-bound DNA from the unbound by washing with binding buffer. Then the bound DNA is nonspecifically eluted by denaturation using urea and heating. To enrich the bound DNA sequences, the eluted DNA pool is amplified by PCR after desalting to remove the urea. We used a fluorescent labelled primer to enable the purification of the fluorescent ssDNA (aptamer) from the PCR product via denaturing PAGE by visualising the fluorescent band and also to facilitate the quantification of the eluted DNA. This cycle of binding, partitioning, amplification and purification is repeated several times to obtain the highest affinity aptamers. Two counter selection steps were performed during the SELEX process. The first counter selection using negative blocked NHS activated beads was introduced after the fifth round in order to eliminate the DNA sequences which binds to the beads matrix. The second counter selection was performed using Hb-beads in order to exclude most of the DNA sequences which bind to Hb and to enable the selection of the HbA1C-specific aptamers. The selected DNA pool from the six round was incubated with Hb-beads followed by washing the beads and incubating the DNA pool collected from the washes with the positive HbA1C beads. To monitor the enrichment of the specific DNA to HbA1C during the selection process, the fluorescence intensity of the eluted DNA from each round was measured. FIG. 1 shows the gradual increase in the DNA recovery with increasing the number of rounds. A small drop in the DNA recovery after the first counter selection with negative beads was observed likely due to the elimination of the sequences that have a certain affinity to the sepharose beads. In fact, the DNA recovery was low until the ninth round and a significant increase in the recovery was observed in the last two round. This increase suggests the enrichment of the HbA1C-specific DNA. Therefore, the DNA pool collected from round 11 was cloned into E coli competent cells. Then, 21 clones were randomly selected for sequencing. Then PRA-LINE software was used to analyse the selected sequences by multiple sequence alignment (Simossis V. A. et. al. 2013) showing significant sequence convergence which indicates the successful enrichment of the DNA pool from round 11. We then grouped the selected sequences into Six different families (A-F) based on their similarities (FIG. 9) and representative sequences from each group were tested for the binding to Hb and HbA1C.

Binding affinity studies and determination of dissociation constants of the aptamers-Hb and -HbA1C complexes: A sensitive and simple electrochemical assay was used to study the binding affinity of the selected aptamers to the Hb and HbA1C proteins. For that, both Hb and HbA1C were individually immobilized on gold electrodes.

Figure 10A:
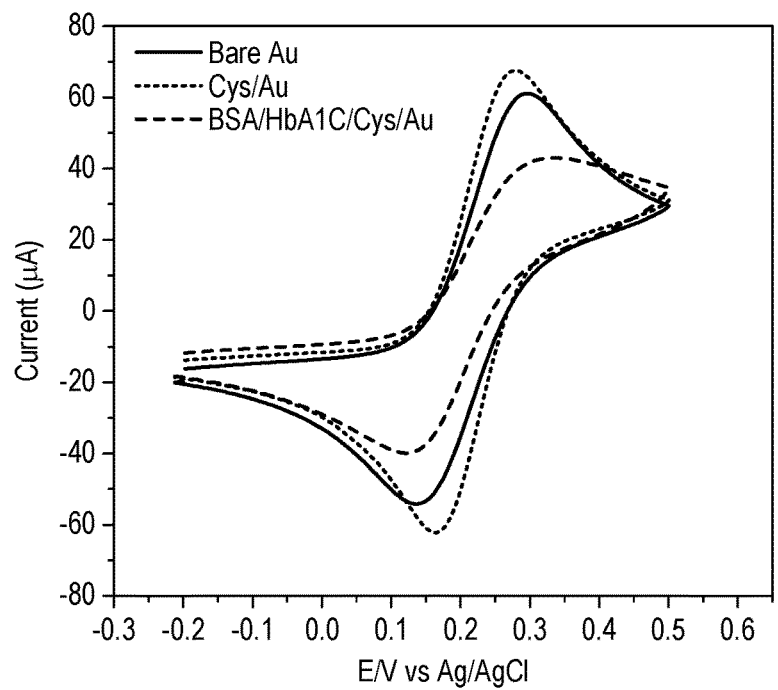
FIG. 10A and FIG. 10B shows Cyclic voltammograms and Nyquist diagrams for bare gold electrodes (black), Cys/Au and after HbA1C immobilization and blocking with BSA recorded in 10 mM $[Fe(CN)_6]^{4-/3-}$ redox probe in PBS, pH 7.4.
Figure 10B:
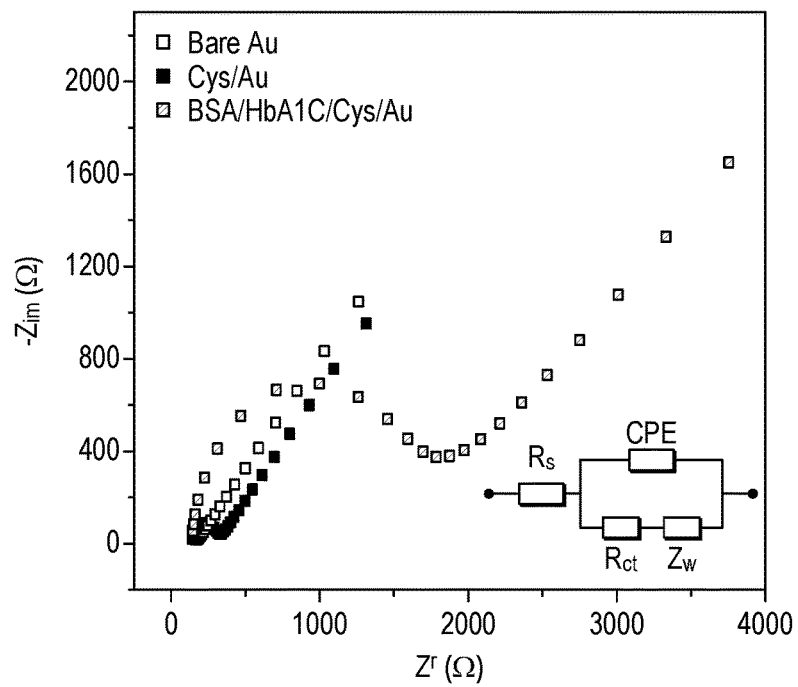
Figure 11A:
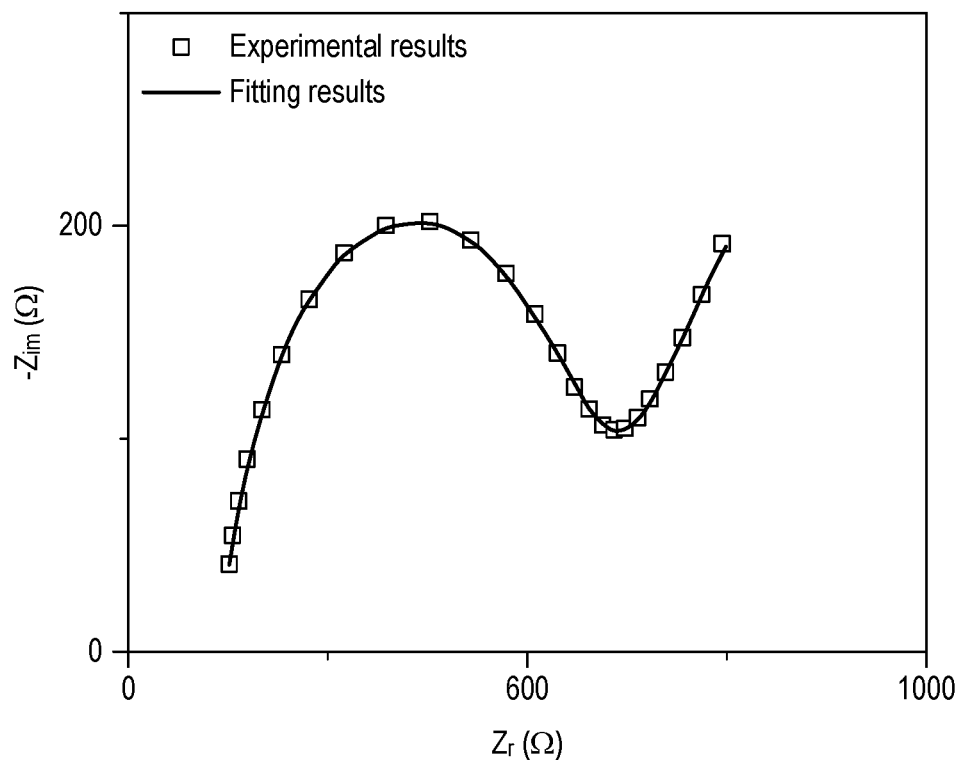
FIG. 11A shows example of a Nyquist plot.
Figure 11B:
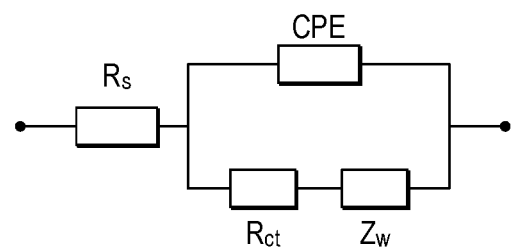
FIG. 11B shows modified Randles equivalent circuit which used to fit the impedance results.

Immobilization of Hb and HbA1C on the gold electrodes: Both Hb and HbA1C proteins were immobilized on gold electrodes via the amine groups of the proteins. The gold surface was first modified via the formation of self-assembled monolayer (SAM) of cysteamine. Then, 1,4-phenylene diisothiocyanate which serves as a bifunctional linker was employed to covalently link the amine groups of the proteins to the terminal amine groups of Cys/Au (FIG. 9) forming carbamide moiety. To confirm the successful modification of the gold electrodes and the immobilization of the Hb and HbA1C proteins, CV and EIS were used (FIGS. 10A and 10B). The Impedance spectra were fitted using modified Randles equivalent circuit (FIGS. 11A and 11B).

Figure 2A:
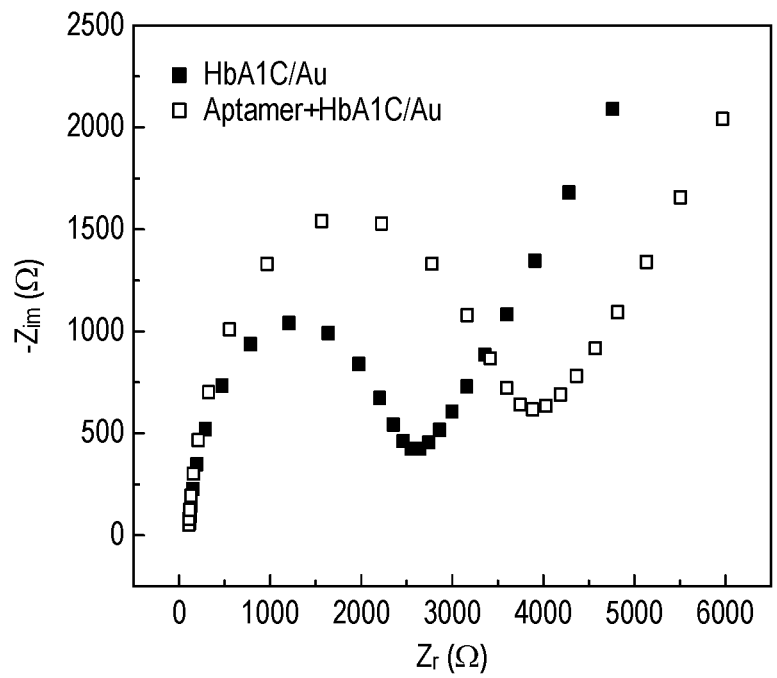
FIG. 2A Example of Nyquist plot of the HbA1C modified gold electrodes before (black) and after (red) aptamer binding.

Binding affinity analysis of the aptamers: Eight representative sequences were subjected to initial binding analysis. Initial screening of the aptamer sequences (G11, G23, G20, G18, G15, G10, G22, G4) was performed using EIS to confirm their successful binding to HbA1C (FIG. 2A).

TABLE 1

Aptamer sequences:

| Seq ID # | aptamer number | Aptamer sequence |
|---|---|---|
| Seq ID #1 | G 4 | GGGCCGACGGGAGGGGGAGGGAGAGCAATACGAGGTGGGATGGCAGATTATGGGTGCACT |
| Seq ID #2 | G 10 | CACCACTCAGCGACATCATATCATGAAAAGCGGAGAGCATCCGTGACGTGTGGTTTGGNT |
| Seq ID #3 | G 11 | CGACACCAGCACACAGACCCGAGACACACGTCAGATCAACAGCGACCGTATCATTGGTTG |
| Seq ID #4 | G 15 | ACGCACACCAGAGACAAGTAGCCCCCCAAACGCGGCCACGGAACGCAGCACCTCCATGGC |
| Seq ID #5 | G 18 | GGCCACAGCAGCCAGTACACCCACCCACCAGCCCCGTCAACGACCTGAACCTGCCCTGTGTG |
| Seq ID #6 | G 20 | GGGGACACAGCAACACACCCACCCACCAGCCCCAGCATCATGCCCATCCGTCGTGTGT |
| Seq ID #7 | G 22 | CGCACACCAGCACACTCAAAAGAACATACAAAGAACGTCGATCCACATACCACGGCTGCC |
| Seq ID #8 | G 23 | GGACACGGCAAAGGGGTATAGCCTACCGGACCGTGGACATGGAATTGTGTGCTGCGTGG |

Figure 2B:
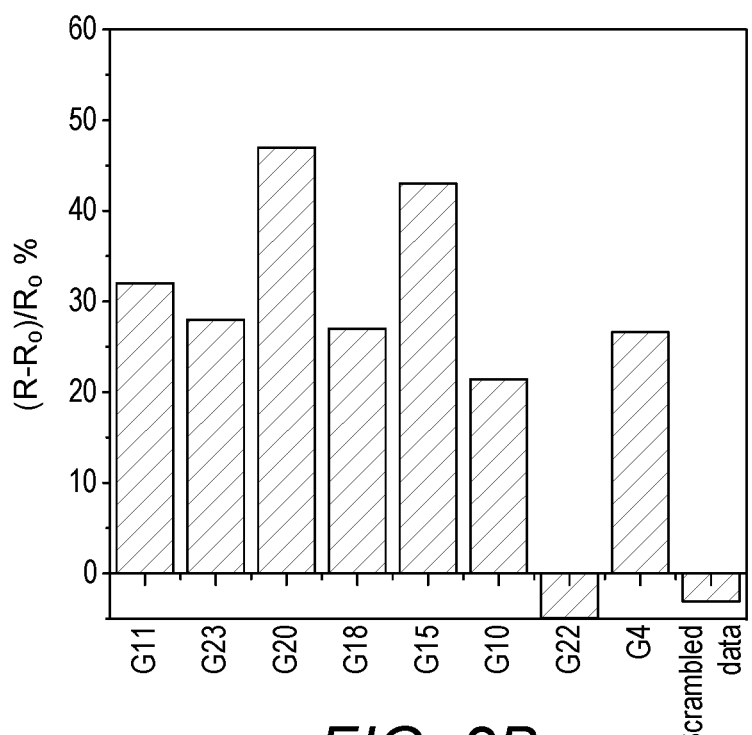
FIG. 2B, a comparative binding analysis was done for the aptamer sequences to HbA1C by monitoring the percentage change of the $R_{CT}$ of HbA1C-modified electrodes upon binding with each aptamer.
Figure 3A:
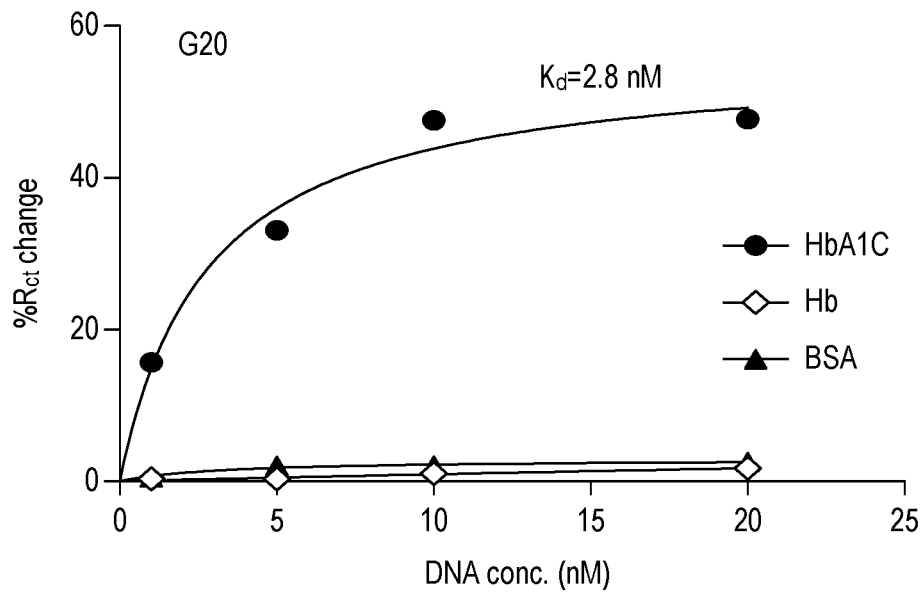
FIG. 3A Binding curves of the selected aptamers G20 with HbA1C and nonspecific proteins and aptamer G15 FIG. 3B with Hb, HbA1C and non specific protein.
Figure 3B:
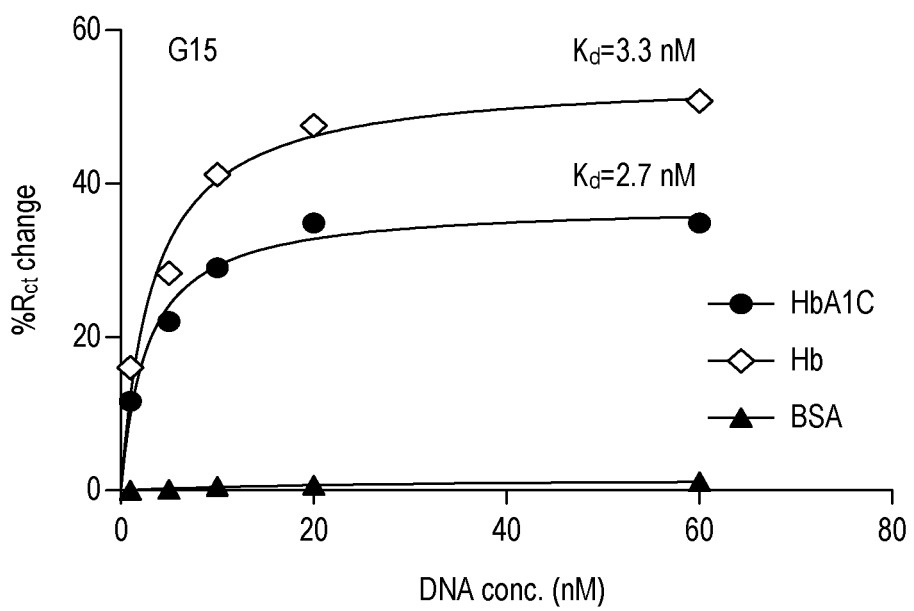

As shown in FIG. 2B, a comparative binding analysis was done for the aptamer sequences to HbA1C by monitoring the percentage change of the $R_{CT}$ of HbA1C-modified electrodes upon binding with each aptamer. A significant change in the $R_{ct}$ after the incubation of most of the tested aptamers with the HbA1C electrodes while no response was obtained with scrambled DNA sequence (control DNA) indicating specific binding of the aptamers to HbA1C. Only one sequences (G22) did not show good binding to HbA1C. The highest change in EIS signal was obtained for aptamers G11, G23, G18, G20, G15, therefore these aptamers were subjected to further analysis to assess their binding affinity. The dissociation constants were determined by incubating different concentrations of the aptamers with Hb and HbA1C-modified electrodes. As shown in FIG. 3, binding curves were obtained by plotting the change in the electron transfer resistance versus the aptamers concentrations. The $K_d$ were then calculated from the binding curve using non linear regression analysis. As shown in Table 1, two different types of sequences were identified and the $K_d$ values of the aptamers were shown to be in the nanomolar range. Four HbA1C-specific aptamers with high affinity and specificity were obtained (G11, G18, G20, G23). It was observed that the aptamer G20 exhibited the highest binding affinity to HbA1C ($K_d$=2.8 nM). However, interestingly, the aptamer sequence G15 showed good binding to both Hb and HbA1C with almost similar $K_d$ of 2.7 and 3.3 nM. The aptamer sequences may be made in full or part of it may be used for binding studies. Thus, from our SELEX screening, an aptamer that bind to the tHb (G15) as well as specific aptamers to HbA1C (G20) were obtained. It is worth mentioning that no significant common motifs between our new selected aptamers and the recently reported aptamers. Moreover, our new aptamers showed higher affinity to Hb and HbA1C than the reported sequences ($K_d$ of 7.6 and 7.3 nM for HbA1C and Hb).

The binding specificity of the HbA1C aptamer (G20) was also confirmed by incubating the HbA1C modified electrode with different concentrations of non glycated Hb and BSA as control. No significant response was obtained for the non specific proteins which indicates excellent specificity of the selected aptamer (FIG. 3). Similarly, the specificity of the tHb aptamer (G15) was verified against BSA as control. The two aptamers, G15 and G20, were then applied for Hb and HbA1C detection a microarray platform.

Voltammetric microarray Aptasensors for HbA1C Detection: The microarray screen printed carbon electrodes (FIG. 4A) were first modified by deposition of AuNPs via electroreduction of gold chloride. FIGS. 4A and 4B shows the scanning electron microscopic (SEM) image of the carbon electrode before and after AuNPs deposition. The two aptamers (G15 and G20) were then immobilized on different AuNPs-modified electrodes on the same chip array by self-assembly of the thiol-modified aptamers. After aptamers immobilization, the electrodes were blocked by MCH to form a mixed monolayer with the thiol-modified aptamers. This step was previously shown to be very important to reduce the nonspecific adsorption of the aptamers on the surface and thus, preserve the conformation of the aptamer (Xiao Y et. al. 2005).

Figure 5A:
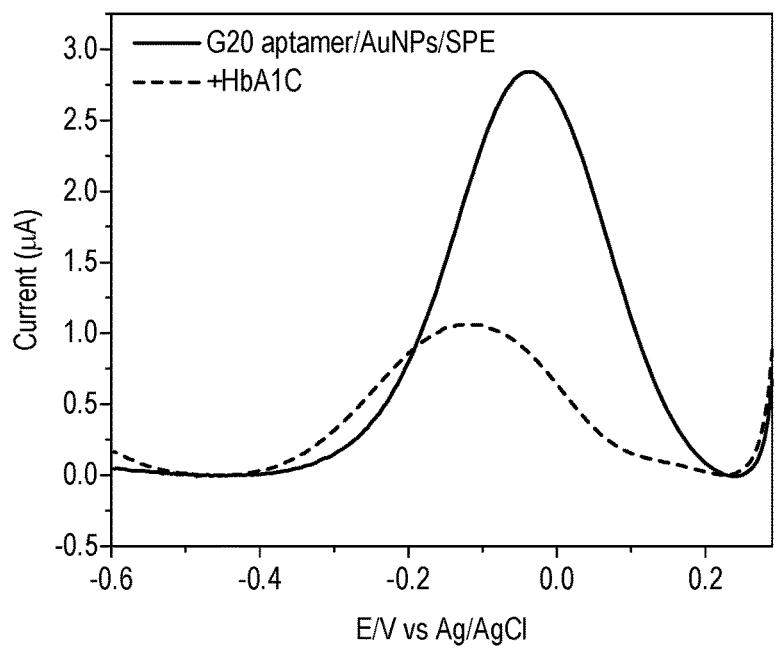
FIG. 5A Example of square wave voltammetry signal of the aptasensor before (black) and after (red) binding with HbA1C.

After the immobilization of the aptamers on the electrodes, SWV was used to monitor the protein binding by measuring the reduction peak current of $[Fe(CN)_6]^{4-/3-}$ redox couple. As shown in FIG. 5A, after HbA1C binding, a decrease in the peak current was observed due to the blocking effect of this bulky protein. This decrease in the SWV current represent the basis of the aptasensor detection signal.

Figure 5B:
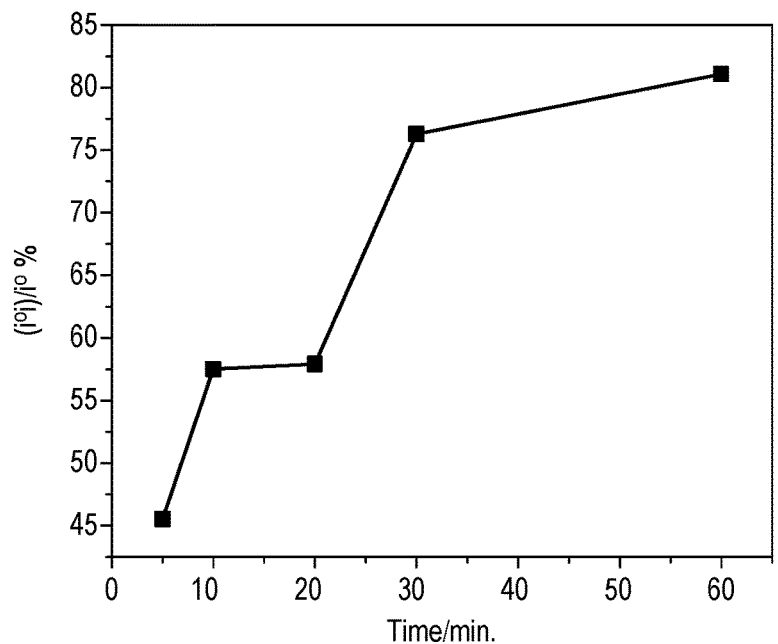
FIG. 5B shows effect of the binding time on the HbA1C aptasensor response signal.

Binding time optimization of the aptasensors: The aptasensor's response)((i–i°/i°%) was measured after incubating 1 µg/ml of tHb and HbA1C on the G15 and G20 modified electrodes, respectively at different time points. As shown in FIG. 5B, the reduction peak current decrease with increasing the incubation time. Maximum response was observed after 30 min incubation with the HbA1C protein. Therefore, 30 min was chosen as the binding time in the subsequent experiments for Hb and HbA1C.

Figure 6A:
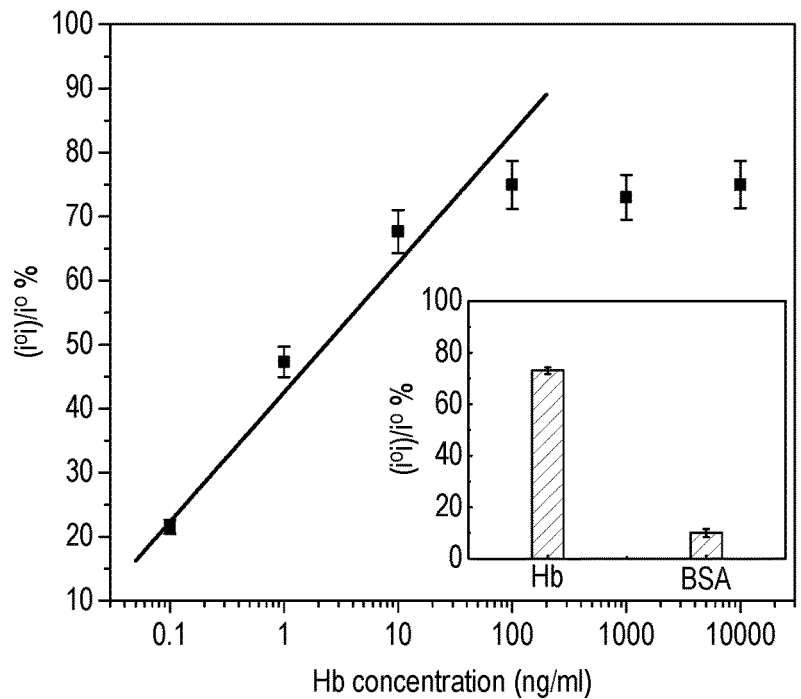
FIG. 6A shows calibration curves for Hb and HbA1C is shown in FIG. 6B. Insets are the specificity studies of the aptasensors against BSA.
Figure 6B:
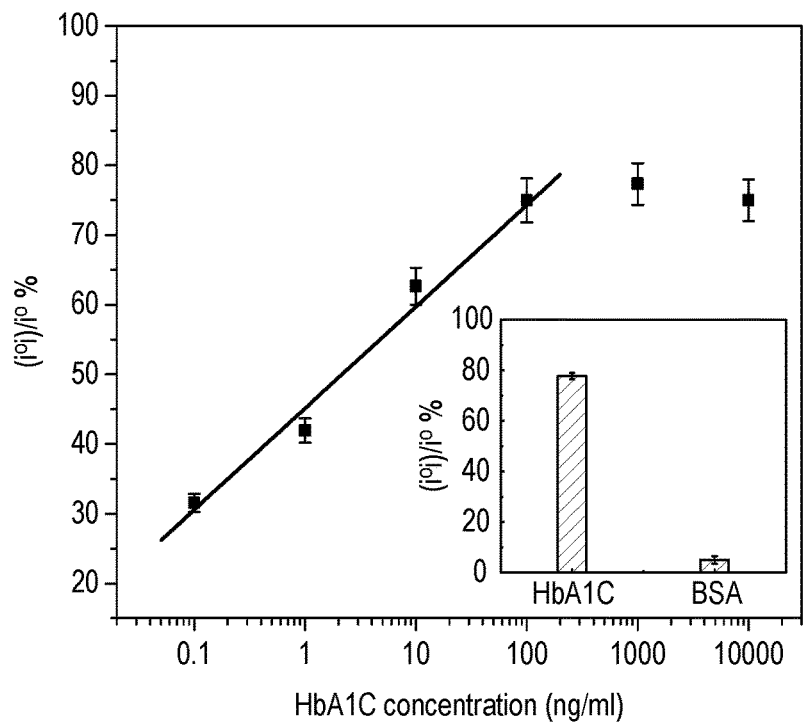

Dose response of the aptasensors: The aptasensors voltammetric response toward tHb and HbA1C was measured in the concentration range of 100 pg/mL to 10 µg/mL. Significant drops in the reduction peak current were observed with increasing concentrations of Hb and HbA1C due to the binding of the proteins to their specific aptamers which blocks the electron transfer as explained above. FIG. 6A and FIG. 6B shows the calibration plots based on the percentage change in the peak current after the Hb (FIG. 6 A) and HbA1C (FIG. 6B) binding. Three independent measurements were done for each data point in order to assess the reproducibility of the aptasensors array. Both HbA1C and tHb aptasensors showed linear response within a concentration range from 100 pg/mL to 100 ng/mL. The linear regression equation of the HbA1C aptasensor is (i°–i)/ i°%=45.0+14.6×log C [ng/ml], R=0.997, with a detection limit (LOD) of 0.2 ng/mL and for the tHb: (i°−i)/i°%=42.5+20.2×log C [ng/ml], R=0.98, with LOD=0.34 ng/ml. The LOD was calculated from $3(S_{y/x}/m)$, where $S_{y/x}$ is the standard error of estimate and m is the slope of the calibration curve. It is worth noting that, these detection limits are lower than the LOD of the commercial ELISA kits as well as than the reported immunosensor microarray platform. The selectivity of the aptasensors were also confirmed by incubating the aptasensors with BSA. As shown in insets of FIG. 6B, a high response signal were observed only when the aptasensors were incubated to their specific protein while no response was obtained with BSA indicating that no effect of nonspecific adsorption was obtained.

Figure 7A:
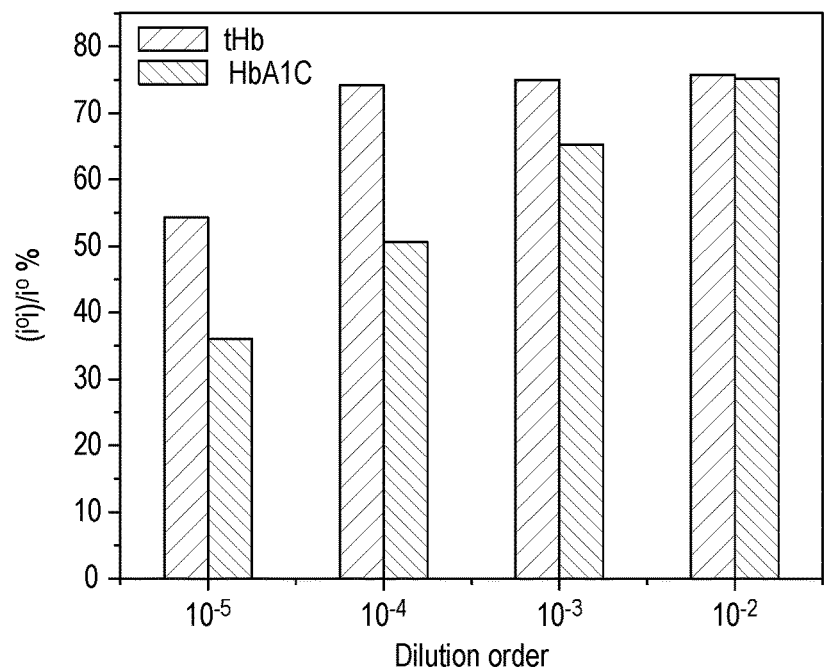
FIG. 7A shows response signals of HbA1C and Hb aptasensors for human blood sample (LN15-08) and FIG. 7B shows linear plot of the sensor response for the HbA1C with four different standard blood samples.
Figure 7B:
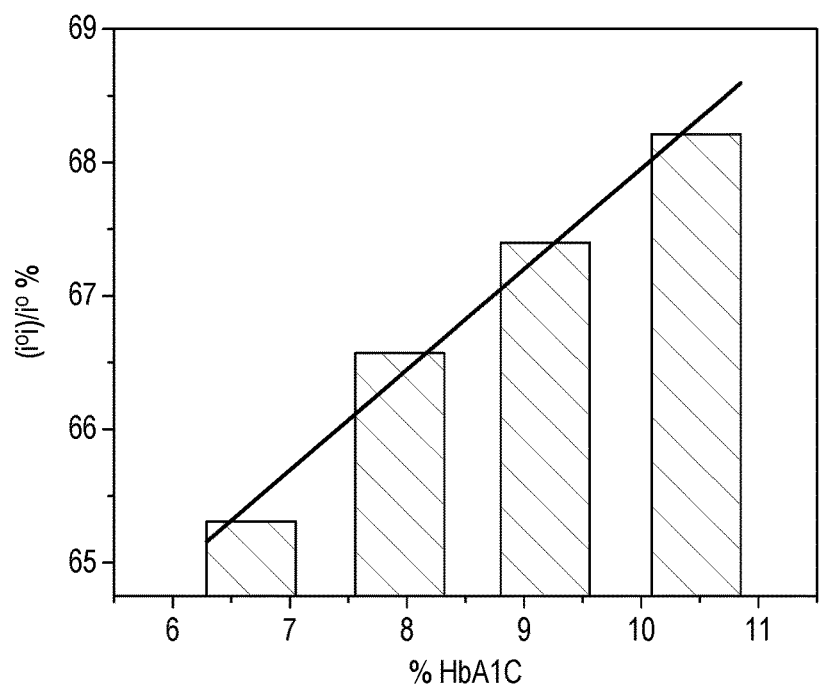

Detection of HbA1C % in whole blood samples: The proposed aptasensor platform was then tested with four quality control blood samples in order to validate the assay. A shown in FIG. 7A, the aptasensor response signal for HbA1C decreases as the standard blood sample (LN15-08) was serially diluted from $10^{-2}$ to $10^{-5}$. However, for the tHb, the aptasensor response decrease for the diluted samples from $10^{-5}$ tole while no further signal change was observed at the higher concentrated samples ($10^{-2}$). When the concentration of the tHb is high, a saturation of the aptasensor occur. Therefore, $10^{-4}$ or $10^{-3}$ should be used for analysis. These results indicates that the proposed aptasensor array platform is able to distinguish and detect tHb and HbA1C over a 3 order of magnitude concentration range. By referring to the calibration curves, the % HbA1C in the sample was calculate to be 6.67% which is in very good agreement with the values given by the college of American pathologist. A linear relationship was also obtained between the % HbA1C and the HbA1C aptasensor response signals within a concentration range of 6.67-10.47% (FIG. 7B). These results confirms the possible applicability of the developed aptasensor array platform to discriminate between diabetic and healthy individuals.

High affinity DNA aptamers for HbA1C and tHb were successfully selected using SELEX after 11 rounds of selection. The tested aptamers bind to HbA1C with dissociation constants in the nanomolar range with the highest affinity aptamer, G20, exhibiting a $K_d$ of 2.8 nM. Another aptamer sequence which showed high binding affinity to tHb with a $K_d$ of 2.7 nM was also selected. The HbA1C and tHb-specific aptamers were then applied for the detection of HbA1C % using a voltammetric aptasensor array platform showing remarkable sensitivity and selectivity. The aptasensor array platform was validated using standard human whole blood samples and demonstrated linearity over wide concentration range. We believe that the developed platform is superior to current methodologies due to the simplicity, stability and lower cost which will facilitates the early and accurate diagnosis of diabetes.

INDUSTRIAL APPLICABILITY

The method and associated detection method is simple, sensitive, specific, rapid, cost-effective. A human blood sample when processed using this method would give accurate and rapid result that will enable the physician to prescribe the right medication and dosage.

---

What is claimed is:

1. A method of using an aptasensor based microarray technology for measuring a parameter in a blood for a diabetic condition, comprising:

coupling purified hemoglobin (Hb) and glycosylated hemoglobin (HbA1C) separately with N-hydroxysuccinimide-activated sepharose beads (NHS) to form a NHS activated bead with Hb and NHS activated bead with HbA1C;

selecting a DNA aptamer sequence in full or part of this sequence against a glycated hemoglobin and total hemoglobin; wherein the DNA aptamer consists of Seq ID #4 and Seq ID #6;

binding the DNA aptamer to the NHS activated bead with Hb and NHS activated bead with HbA1C;

immobilizing the DNA aptamer bound NHS activated bead with Hb and NHS activated bead with HbA1C to gold electrode to form an aptamer array;

adding a whole human blood after dilution to the aptamer array;

incubating the aptamer array with the whole blood diluted sample for 30 minutes at room temperature and washing with a buffer solution to remove unbound whole blood sample; and measuring a voltametric response for a concentration of a total hemoglobin and glycated hemoglobin in the whole blood using the sensing platform to estimate the said concentration of total hemoglobin and glycated hemoglobin as the parameter for the diabetic condition of a patient.

2. The method of claim 1, wherein the dilution of the whole blood is done sequentially using a deionized water and a binding buffer.

3. The method of claim 1, wherein the aptamer having a sequence in full or part of it is Seq ID#4.

4. The method of claim 1, wherein the aptamer having a sequence in full or part of it is Seq ID#6.

5. A method of using an aptamer sequence for measuring a hemoglobin and glycosylated hemoglobin in a whole blood in a diabetic person, comprising:
    creating an aptamer array of DNA in full or part of it consisting of Seq ID #4 and Seq ID #6;
    contacting the aptamer array with a whole blood sample of a human being; and
    estimating the concentration of a conjugate of the aptamer and a hemoglobin and glycosylated hemoglobin that is bound to the aptamer of Seq ID #4 and Seq ID #6 using a sensing platform for the diagnosis of the disease.

6. An aptamer array containing essentially Seq ID #4 and Seq ID #6 sequences to detect a specific parameter in a human whole blood using a sensing platform.

7. The aptamer array of claim 6, wherein the specific parameter is a total hemoglobin and glycated hemoglobin.

8. The aptamer of claim 6, wherein the Seq ID#4 is used for a total hemoglobin detection.

9. The aptamer of claim 6, wherein the Seq ID#6 is used for a glycated hemoglobin detection.

10. The aptamer array of claim 6, wherein the sensing platform is at least one of an optical, electrochemical, mass-sensitive, thermal sensor or any other type of sensing device.

11. The aptamer array of claim 6, wherein the aptamer array has a gold nanoparticle.

12. The aptamer array of claim 10, wherein the sensing platform is electrochemical using a squarewave voltammetry measurements to detect the specific parameter.

* * * * *